United States Patent
Trott

[11] Patent Number: 5,833,246
[45] Date of Patent: Nov. 10, 1998

[54] CENTRIFUGAL CHUCK FOR SURGICAL HANDPIECE

[75] Inventor: A. Frank Trott, Largo, Fla.

[73] Assignee: Linvatec Corporation, Largo, Fla.

[21] Appl. No.: 851,900

[22] Filed: May 6, 1997

[51] Int. Cl.$^6$ .................................................. B23B 31/14
[52] U.S. Cl. ......................... 279/131; 433/127; 606/180
[58] Field of Search ........................... 279/131; 433/127; 606/80, 180

[56] References Cited

U.S. PATENT DOCUMENTS

| | | | |
|---|---|---|---|
| 2,857,167 | 10/1958 | Smith | 279/106 |
| 2,920,894 | 1/1960 | Kreinick | 279/2 |
| 3,467,404 | 9/1969 | Sloan | 279/66 |
| 3,573,876 | 4/1971 | Powell | 279/1 C |
| 3,625,528 | 12/1971 | Sage | 279/1 C |
| 3,692,319 | 9/1972 | Taylor | 279/1 C |
| 3,709,508 | 1/1973 | Dudley | 279/1 C |
| 3,975,029 | 8/1976 | Benjamin | 279/1 C |
| 4,234,201 | 11/1980 | Sorensen | 279/77 |
| 4,572,525 | 2/1986 | Feldmeier et al. | 279/1 C |
| 4,709,512 | 12/1987 | Okubo et al. | 51/237 R |
| 5,634,933 | 6/1997 | McCombs et al. | 606/180 |

Primary Examiner—Steven C. Bishop
Attorney, Agent, or Firm—Gene Warzecha

[57] ABSTRACT

A centrifugal chuck for a surgical handpiece is adapted to automatically engage a surgical instrument so it may be driven by the handpiece. The centrifugal chuck comprises a pivotable trunnion body situated within a hollow drive shaft, the trunnion body having a throughbore coaxially aligned with the axis of the hollow drive shaft in order to receive the shaft of the surgical instrument. The trunnion body is secured to a pair of lever arms symmetrically situated about the exterior of the drive shaft, the lever arms extending in opposite proximal and distal directions from the pivotable attachment of the trunnion body to the drive shaft. Rotation of the drive shaft causes radially outward movement of the lever arms thereby misaligning the throughbore of the trunnion body relative to the drive shaft in order to frictionally engage the shaft of the surgical instrument. A spring member integrally formed with each lever arm maintains a predetermined bias on the trunnion body in order to provide a predetermined minimum amount of friction to enable the instrument shaft to be retained within the handpiece at speeds below those at which the centrifugal forces become operative. The invention also resides in the method of attaching a surgical instrument to a handpiece utilizing a centrifugal clutch.

9 Claims, 4 Drawing Sheets

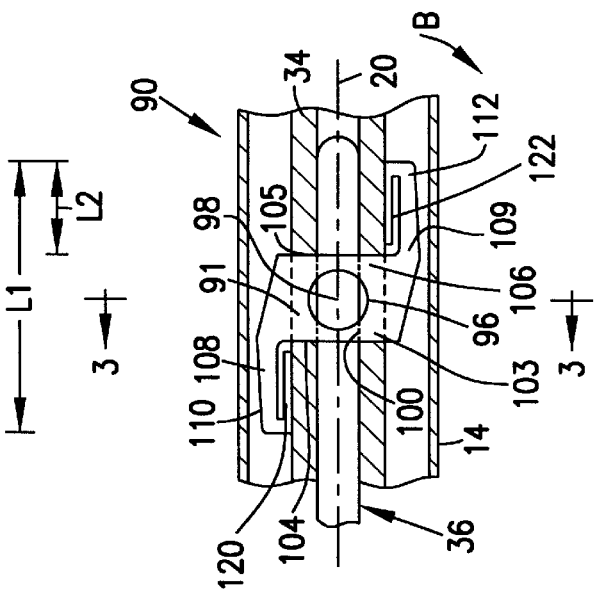
FIG. 2
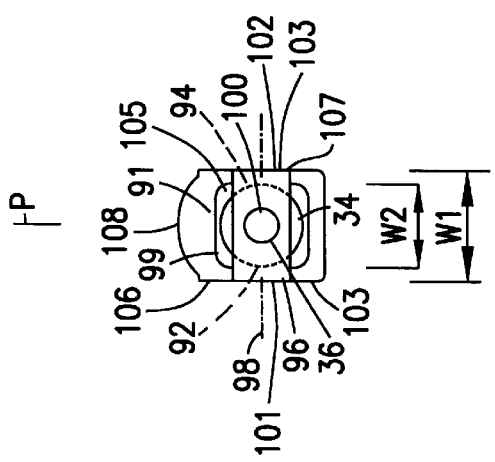
FIG. 3
FIG. 4

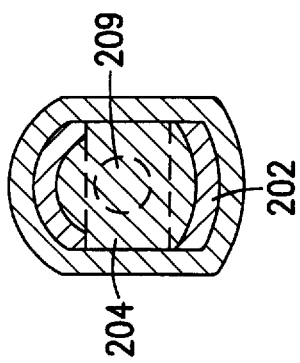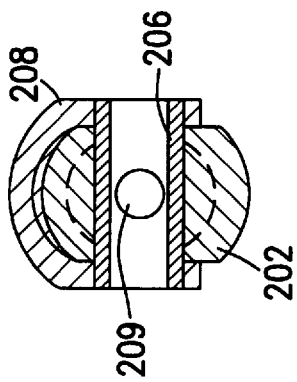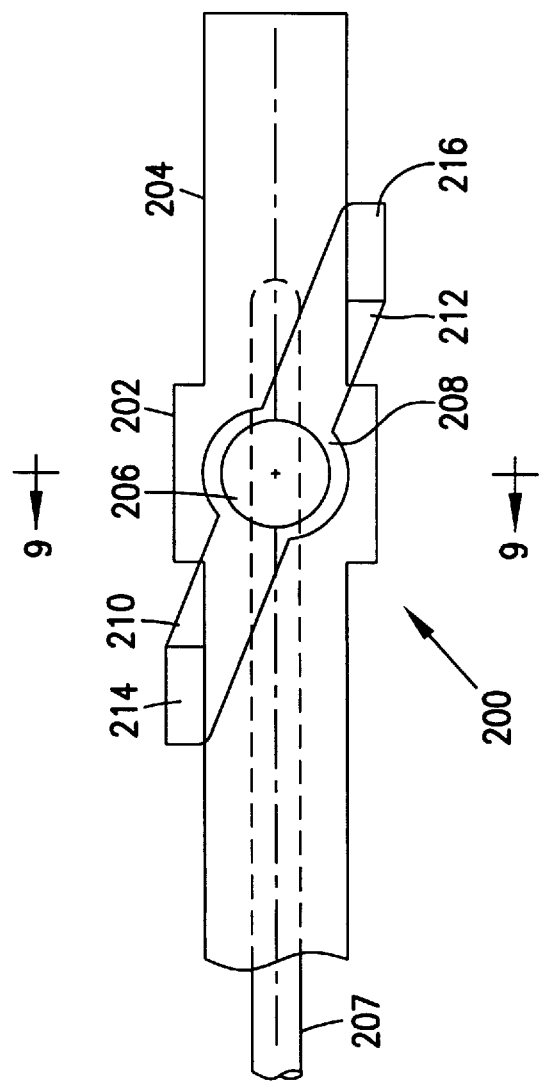

CENTRIFUGAL CHUCK FOR SURGICAL HANDPIECE

BACKGROUND OF THE INVENTION

1. Field of the Invention

This invention relates to a chuck device for holding a tool shaft in a surgical handpiece. More particularly, this invention relates to a centrifugally operated chuck for holding an axially aligned surgical instrument in a pencil-type pneumatic surgical handpiece.

2. Description of the Prior Art

Surgical handpieces are used to drive surgical instruments such as drills, blades, burrs, etc. in a variety of motions. The handpieces are powered by a variety of sources (pneumatic, electric, etc.) and are produced in a variety of shapes chosen to best accommodate the device to a particular surgical procedure. Since each handpiece generally accepts a range of instruments, a chuck device is used to grip the instrument so it may be driven in the selected manner. For instruments such as drills which have elongated shafts which must be driven in a rotary motion, a prior art handpiece is often provided with a chuck which has a plurality of circumferentially arranged movable jaws which are somehow manually tightened around the instrument shaft. Sometimes a separate wrench or other tool is necessary to tighten the chuck.

Such devices have some disadvantages associated with relying on a separate manual operation and a separate tool to tighten a chuck: not only are extra steps required prior to use, but the necessary tools just add to clutter in the operating room. It would be preferable to simplify the chuck to automatically engage and grip the instrument shaft. While centrifugal chucks are capable of such operation, such chucks are known to be used primarily only in large machine tools since they utilize weighted members which move in a single, transverse plane normal to the shaft axis. This makes such devices unsuitable for miniaturization to the size necessary for surgical instruments, particularly pencil-type handpieces.

While there would be a benefit to automatic chucking mechanisms in small surgical handpieces, in addition to the need to keep such chucking mechanisms small, there is also the need to assure that the instrument is always engaged so it does not fall out of the handpiece. That is, a centrifugal chuck must engage the instrument shaft even when it is not rotating.

U.S. Pat. No. 3,573,876 (Powell) does disclose a centrifugal chuck for a small surgical drill such as a dental drill. The Powell device utilizes two semi-cylindrical pieces transversely mounted in a handpiece drive shaft. The pieces have throughbores to receive the instrument shaft in alignment with the drive shaft axis. Upon rotation of the drive shaft, the two pieces move transversely apart from each other causing their throughbores to move in opposite directions, thereby gripping the instrument shaft extending therethrough. A pair of O-rings imparts a slight misalignment to the throughbores to create a minimal amount of tension to hold the instrument shaft even when the drive shaft is not being rotated. The gripping forces provided by this device may be increased by the subject invention and the complexity of the device may be decreased. Furthermore, the O-rings necessitate periodic replacement due to their well-known tendency to deteriorate over time, especially in the harsh environment of surgical devices. It would also be preferable to apply a pre-load to a centrifugal chuck without using additional, discrete elements.

It is, therefore, an object of this invention to produce an automatic chuck for use with a pencil-type surgical handpiece.

It is also an object of this invention to produce an automatic chuck which is centrifugally operated.

It is also an object of this invention to produce a centrifugally operated chuck which has a maximum diameter less than that of prior art centrifugal chucks.

It is yet another object of this invention to produce a centrifugally operated chuck which is adapted to engage an instrument shaft even when stationary. It is a further object to produce such a device with a fewer discrete components than prior art devices.

SUMMARY OF THE INVENTION

These and other objects of the invention are achieved by the preferred embodiment disclosed herein which is a centrifugal chuck apparatus for coaxially securing a tool shaft to a rotatable hollow driving shaft comprising a hollow drive shaft having an axis; a body having an axis and a throughbore for receiving the tool shaft therethrough, the throughbore having an axis transverse to the body axis; a first lever arm extending proximally a first predetermined distance from the body on a first lateral side of the drive shaft axis; a second lever arm extending distally a second predetermined distance from the body on a second lateral side of the drive shaft axis, diametrically opposite the first lateral side; and means for pivotably securing the body to the drive shaft to enable the body to move about its axis, in response to centrifugal force thereon, between a first position in which the throughbore axis is substantially coaxial with the axis of the drive shaft and a second position in which the first throughbore axis is misaligned relative to the axis of the drive shaft to thereby frictionally engage the tool shaft.

The invention also resides in the method of for coaxially securing a tool shaft of a surgical instrument within the hollow drive shaft of a surgical instrument comprising the steps of providing a trunnion body on the drive shaft, the body having an axis and a throughbore for receiving the tool shaft therethrough, the throughbore having an axis substantially coaxial with the axis of the drive shaft; pivotably attaching the body to the drive shaft to enable the throughbore axis to move about its axis, in response to centrifugal force; securing to diametrically opposing lateral sides of said body a lever arm and extending said lever arms in opposite directions from each other to apply a centrifugal force to said body about its axis upon rotation of the drive shaft; inserting a tool shaft into the drive shaft and the throughbore; and rotating the drive shaft to turn the body about its axis to thereby centrifugally secure the tool to the body.

BRIEF DESCRIPTION OF THE DRAWINGS

FIG. 2 is a side elevational view of a portion of FIG. 1 showing the centrifugal chuck engaged with an instrument shaft.

FIG. 3 is a sectional view of FIG. 2 taken along the line 3—3.

FIG. 4 is a cross-sectional view of the components of FIG. 2 showing the parts thereof partially disassembled.

FIG. 7 is another alternate embodiment of a centrifugal chuck constructed in accordance with the principles of this invention.

FIG. 8 is a right side of FIG. 7.

FIG. 9 is a sectional view of FIG. 7 taken along the line 9—9.

DESCRIPTION OF THE PREFERRED EMBODIMENT

Figure 1:
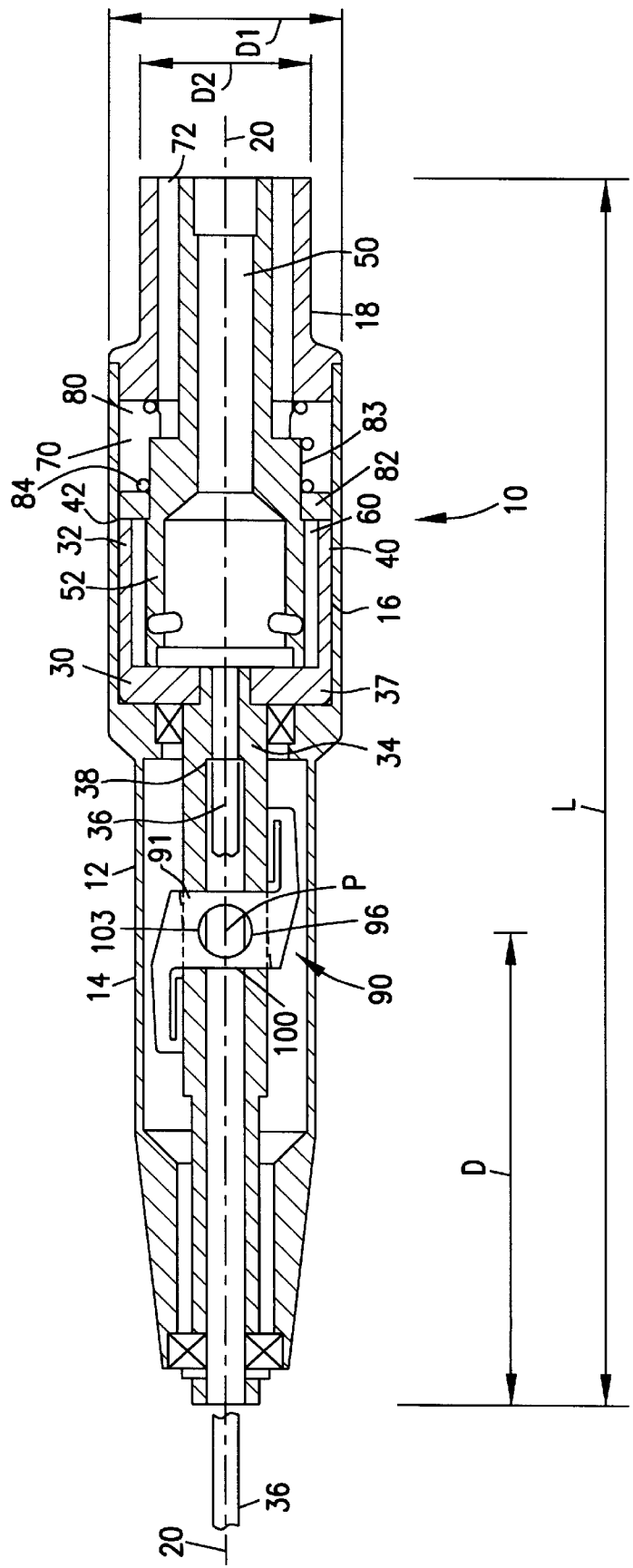
FIG. 1 is a schematic side elevational view in crosssection of a surgical handpiece constructed in accordance with the principles of this invention.

The surgical handpiece 10 shown in the drawings is in large part the subject of a separate application co-pending herewith, assigned to the assignee hereof and incorporated by reference herein. As shown in the drawings, surgical handpiece 10 is a pencil-type pneumatic handpiece comprising a tubular housing 12 having a distal portion 14, a central portion 16 and a proximal portion 18 all aligned along a common axis 20. Tubular housing 12 also serves as the body of the handpiece to be gripped by a user. This handpiece is described here in order to describe an embodiment of a surgical handpiece in which the subject invention may be used. It will be understood, however, that the invention is suitable for a variety of handpieces. Rotatably received within housing 12 is a rotor assembly 30 comprising an open ended, cantilevered turbine body 32 and a hollow output shaft 34 extending distally from the turbine body. An instrument shaft 36 (such as a drill bit) may be received in hollow output shaft 34 and seated against its proximal end 38. The proximal portion 18 is connected to a dual lumen hose (not shown) for supplying to the handpiece a pressurized fluid and for conveying from the handpiece the exhaust fluid.

Turbine body 32 has a distally situated, transverse end wall 36 and an imperforate cylindrical wall 40 extending proximally from end wall 36. A rim 42 is situated at the proximal end of the turbine body and the interior of the rim 42 is open so that wall 40 thus encloses an interior chamber bounded by the cylindrical wall and the end wall. Axially aligned fluid inflow conduit 50 directs pressurized fluid from a pressure source (not shown) to the interior chamber of turbine body 32 via an axially aligned, non-rotating dispersing cap 52 adapted to fit closely within the cylindrical interior chamber and to divert the fluid flow from an axial direction to a transverse direction toward the interior surface of the cylindrical wall 40. Dispersion cap 52 is provided with a plurality of circumferentially arranged ports adapted to not only divert the fluid flow transversely but, by being inclined at a predetermined angle relative to a radial line of the turbine body, the slots impart a tangential element to the flow direction. The interior surface of the turbine body is provided with a plurality of longitudinally extending arcuate channels 60, each of which has a closed distal end adjacent end wall 36 and an open proximal end adjacent rim 42. The open ends of the channels direct exhaust fluid into an annular chamber 70 from which the exhaust is directed through a plurality of annularly arranged channels 72 into an annular exhaust channel concentrically situated about a fluid inflow conduit.

The handpiece is provided with a pneumatic braking mechanism 80 in order to stop the rotation of rotor 30 below a predetermined fluid pressure. Braking mechanism 80 comprises an annular friction pad 82 having an outside diameter approximately equal to that of the open end of the turbine body and an inner diameter to engage a hexagonally profiled outer surface of the inflow conduit 83. Pad 82 is biased distally, against the open end of turbine body by a spring 84. Once a predetermined minimum amount of fluid pressure is built up within the inflow fluid conduit and, therefore, within the interior chamber of turbine body, brake pad 82 will be pushed proximally, thereby allowing the rotor to rotate. Fluid will thereafter flow around the pad and exit through the exhaust manifold.

An automatic centrifugal chuck device 90, best seen in FIGS. 2–4, is used to automatically secure instrument shaft 36 within the output shaft 34. Chuck device 90 comprises a trunnion body 91 pivotably attached to output shaft 34 at pivot point P. Actually, point P represents the transverse pivot axis 98 about which the trunnion body pivots, as will be understood below. In the preferred embodiment point P is situated at a distance D on the order to 1.6 inches (40.64 mm) from the distal tip of the handpiece. Instrument shaft 36 is long enough to extend into the hollow output shaft at least some predetermined distance which is long enough to pass the pivot point P. Trunnion body 91 comprises a trunnion shaft 96 adapted to be received within the drive shaft and associated lever arms symmetrically arranged on the exterior of the drive shaft. At point P the wall of output drive shaft 34 is provided with a pair of diametrically opposed apertures 92, 94 (best seen in FIG. 3) which pivotably receive trunnion shaft 96 in an orientation with its axis 98 transverse to and intersecting the output shaft axis 20. Thus, trunnion shaft 96 is rotatable relative to the drive shaft. Trunnion shaft 96 has a longitudinally aligned bore 100 which, in one configuration of the elements as shown in FIG. 2, is aligned with (i.e. Substantially coaxial with) the output shaft axis 20. The diameter of bore 100 is sized to create a slip fit with the instrument shaft 36. Each end 101, 102 of the trunnion shaft is fixedly secured to a central body 103 which lies on the exterior of drive shaft 34 and within distal housing portion 14. In the embodiment shown, body 103 is a generally rectilinear frame having distal and proximal openings 104, 105 to receive drive shaft 34 and opposed sides 106, 107 to which trunnion ends 101, 102 are fixedly secured. The area 99 adjacent pivot P and between the central body and drive shaft 34 may be open as shown in FIG. 3 or may be enlarged by a boss as will be understood below. In either event, some clearance space must remain between the drive shaft and the central body so the latter may pivot about axis 98. Lever arms 108, 109 lie on opposite lateral sides of axes 98 and 20 and extend along the exterior of drive shaft 34 distally and proximally from top and bottom sides of body 103, respectively, and have mass portions 110, 112 at their respective ends. The mass portions may be provided with additional weight (not shown) but, if the length of each lever arm extends far enough from axis 98 to create a sufficient moment arm about axis 98, the mass of material inherently in portions 110, 112 will be enough to create adequate holding power. As the output shaft 34 rotates about axis 20, body 103 will rotate about axis 98 and cause the lever arms and mass portions to move radially outwardly thereby rotating trunnion shaft 96 about axis 98, thus causing the trunnion bore 100 to become misaligned relative to the drive shaft bore axis 20 thereby squeezing shaft 36 of the instrument. In other words, trunnion body 91 moves from a position in which its bore 100 is substantially coaxial with axis 20, to a position in which it is misaligned. Since the degree of misalignment in these positions may be very small if the clearances are tight, the positions are not explicitly shown in the drawings. However, one may refer to FIGS. 1 and 2 to see the range of pivotal motion to which trunnion body 91 may be subjected. Because of the length of lever arms 108, 109, the forces exerted on shaft 36 by trunnion shaft 96 will be much larger than available in prior art devices of comparable size. While body 91 is shown separate from trunnion 96, it will be understood that the lever arms could be connected directly to the ends of the trunnion shaft, thus eliminating a central body per se.

Referring briefly to FIG. 4, instrument shaft 36 is shown disassembled from output drive shaft 34 to show the normal unbiased configuration of chuck 90. Spring limbs 120 and 122 are formed adjacent mass portions 110, 112, respectively, to apply a pre-loading force to bias trunnion shaft 96 against shaft 36 at speeds below a predetermined speed at which the centrifugal force becomes operative to pivot the trunnion body about its axis. The spring limbs are formed so as to have their distal tips 124, 126 contact the exterior surface of drive shaft 34 in order to impart to body 90 and trunnion 96 a rotational force in order to cause trunnion bore 100, normally aligned along its axis 130, to be misaligned from axis 20 of the drive shaft 34 by a predetermined angle A (exaggerated in FIG. 4). Thus, it will be noted that the distal end 132 and proximal end 133 of bore 100 will be spaced away from the internal surface 134 of the bore of drive shaft 34. The spring limbs tend to bias ends 132, 133 inwardly in order to create a friction fit with an instrument shaft at speeds below a predetermined level when centrifugal force is inadequate. Instrument shaft 36 is provided with a lead-in or chamfered tip 136 in order to enable the instrument shaft to be inserted into the bore of drive shaft 34 and past the interference created by the inwardly positioned end 132. Once the instrument shaft is inserted past this point, the chuck body 91 will be positioned essentially as shown in FIG. 2 with the spring limbs more aligned with and pressing against the outer surface of drive shaft 34. It will be understood that in this position the spring limbs push against the external surface of drive shaft 34 to impart to throughbore 100 a force in direction B about the trunnion axis 98. Even without rotation of drive shaft 34, this force will be sufficient to push trunnion ends 132, 133 inwardly to frictionally engage instrument shaft 36 and thereby retain it within drive shaft 34. The interior surface of throughbore 100 may be roughened or otherwise treated to enhance this frictional engagement. This may be especially helpful if the trunnion shaft is made of plastic. Note that trunnion body 91 is a single, uniquely shaped integral piece which contains central body 103, lever arms 108, 109, mass portions 110, 112 and spring limbs 120, 122 and has a pair of opposed apertures to receive a separate trunnion shaft. Trunnion body 91 and shaft 96 could be made of metal, plastic or other non-metallic components. In the preferred embodiment, the length L of the handpiece 100 may be on the order of 96.5 mm (3.8 inches) and the diameter D1 may be 19.05 mm (0.75 inches) while D2 could be 14.22 mm (0.56 inches). The width W1 of trunnion body 91 may be on the order of 7.671 mm (0.302 inches) and the width W2 may be on the order of 6.401 mm (0.252 inches). The overall length L1 of the trunnion body may be on the order of 20.93 mm (0.824 inches) while the length L2 may be on the order of 7.112 mm (0.280 inches).

Figure 6:
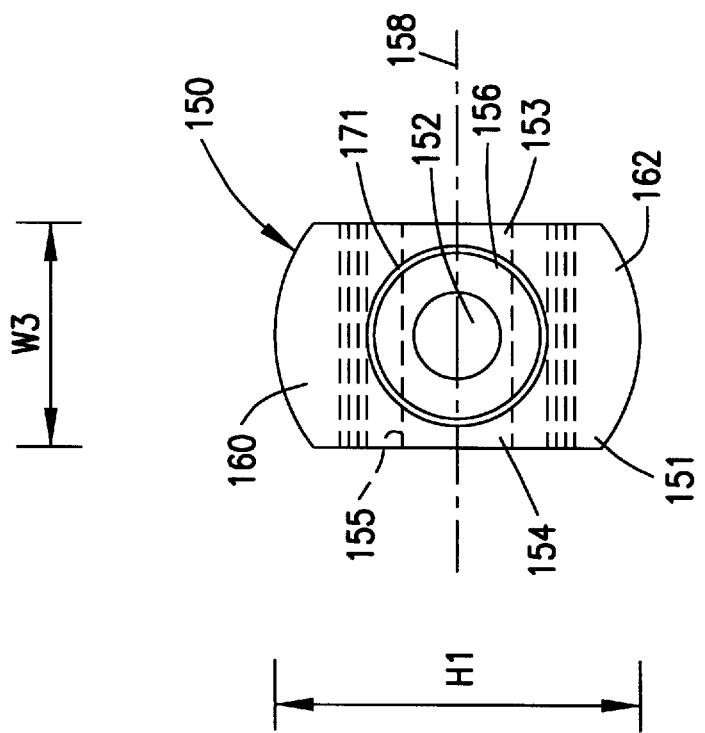
FIG. 6 is a side view of FIG. 5.
Figure 5:
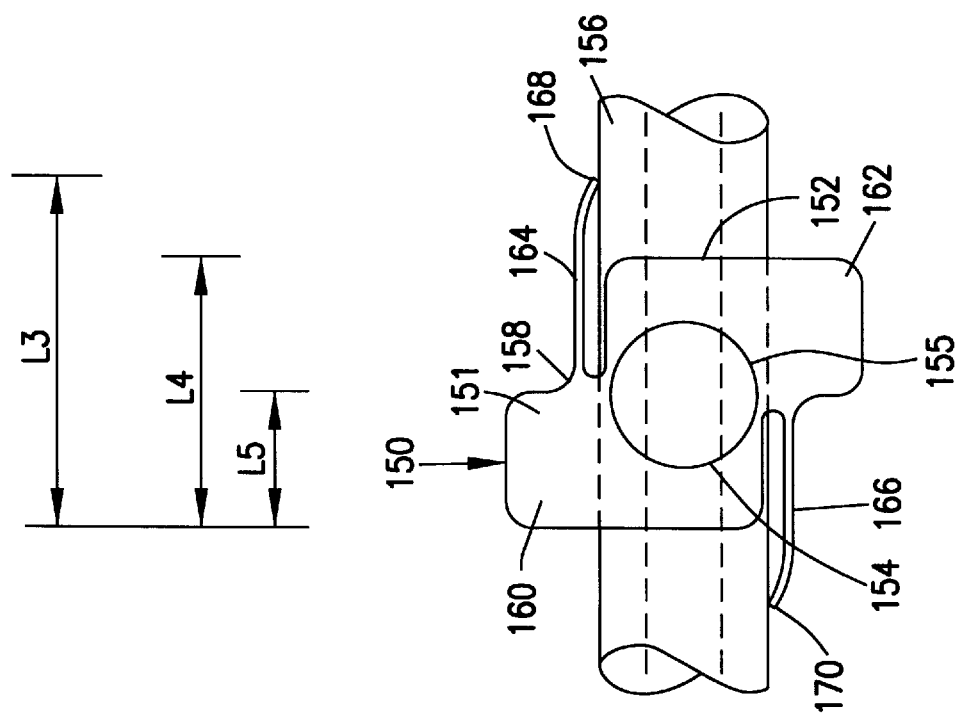
FIG. 5 is an alternate embodiment of a centrifugal chuck constructed in accordance with the principles of this invention.

An alternate embodiment of the automatic chuck is shown in FIGS. 5 and 6 as chuck 150. Chuck 150 operates on similar principles to chuck 90 although the structure of the trunnion body 151 is somewhat different. Chuck 150 has a central body for receiving a trunnion shaft 155, longitudinally aligned bore 152 for receiving an instrument drive shaft and transverse ends 153, 154 fixedly secured to opposing sides of the central body. The trunnion shaft is, similarly to the previous embodiment, pivotably situated within diametrically opposed apertures formed in the wall of drive shaft 156 and is pivotable about its axis 158 relative to the drive shaft. A distally extending lever arm 160 is situated on one lateral side of the drive shaft and a proximally extending lever arm 162 is situated on the other side of the drive shaft diametrically opposite lever arm 160. Integrally formed leaf spring members 164 and 166 extend proximally and distally, respectively, relative to lever arms 160 and 162. The distal tips 168 and 170 of the spring members are formed to contiguously engage the outer surface of drive shaft 156 in order to bias the trunnion body into a predetermined degree of misalignment between the longitudinal axis of its throughbore and the longitudinal axis of the drive shaft 156. A space 171 is shown between drive shaft 156 and an interior bore of the trunnion body. This interior bore receives the drive shaft and the clearance space permits the trunnion body to pivot about axis 158. A variety of other centrifugal chuck bodies could be devised incorporating integral spring biasing mechanisms. The leaf springs 164, 166 may extend the full width of the trunnion body, as shown in FIG. 6, or just over the central portion. The length L3 of trunnion body 151 may be on the order of 9.754 mm (0.384 inches), L4 may be on the order of 7.341 mm (0.289 inches), and L5 may be on the order of 3.759 mm (0.148 inches). The width W3 may be on the order of 6.096 mm (0.24 inches) while the height Hi may be on the order of 9.906 mm (0.39 inches).

Another alternative embodiment of the automatic chuck is shown in FIGS. 7–9, without an integral spring biasing mechanism, as chuck 200 which is mounted on an enlarged boss 202 of drive shaft 204. Such an enlarged boss may be helpful in some configurations to strengthen the drive shaft at the point of attachment of the chuck in the light of material removed to form the transverse, trunnion receiving apertures. A trunnion shaft 206 is transversely, pivotably situated through drive shaft 204 and its ends are fixedly secured to central body 208. Shaft 206 has a longitudinal throughbore 209 for receiving instrument shaft 207. Lever arms 210, 212 extend distally and proximally and mass portions 214, 216 are secured to the distal ends of the lever arms. The operation of this embodiment is analogous to the previously described embodiments.

While the central body (such as 103) was shown to be separate from trunnion shaft 96 (such as in all embodiments), it will be understood that the two elements could be formed together, for example in two symmetrical halves joined along a longitudinal, axial plane, or could be formed otherwise. As another example, two symmetrical halves such as those just mentioned could be formed without joining the halves and even leaving a gap between them, the gap being aligned in an axial plane perpendicular to the transverse axis of the trunnion shaft. As shown in FIG. 3, the symmetrical halves could be formed about plane P with the components attached to body side 106 being non-contiguous to those components attached to body side 107. This would allow one member having one-half of the body, lever arms and trunnion shaft to be inserted into drive shaft aperture 92, and a symmetrical member to be inserted through aperture 94, thus simplifying assembly.

It will be understood by those skilled in the art that numerous improvements and modifications may be made to the preferred embodiment of the invention disclosed herein without departing from the spirit and scope thereof.

What is claimed is:

1. A centrifugal chuck apparatus for coaxially securing a tool shaft to a rotatable hollow driving shaft comprising:

a hollow drive shaft having a first longitudinal axis;

a trunnion shaft body having a transverse axis and a throughbore for receiving the tool shaft therethrough, said throughbore having a second longitudinal axis transverse to said body axis;

a first lever arm fixedly joined to said trunnion shaft body and extending proximally a first predetermined distance from said body on a first lateral side of said drive shaft axis;

a second lever arm fixedly joined to said trunnion shaft body and extending distally a second predetermined distance from said body on a second lateral side of said drive shaft axis, diametrically opposite said first lateral side; and means for pivotably securing said trunnion shaft body to said drive shaft to enable said shaft body to move about said transverse axis, in response to centrifugal force thereon, between a first position in which said throughbore second longitudinal axis is substantially coaxial with the axis of said drive shaft and a second position in which said throughbore second longitudinal axis is misaligned relative to the axis of said drive shaft to thereby frictionally engage said tool shaft.

2. A centrifugal chuck apparatus according to claim 1 further comprising:

spring means for biasing said trunnion body about its transverse axis.

3. A centrifugal chuck apparatus according to claim 2 further comprising:

a first leaf spring member attached to the distal end of said first lever arm and extending distally a first predetermined distance from its point of attachment; and a second leaf spring member attached to the distal end of said second lever arm and extending proximally a second predetermined distance from its point of attachment.

4. A centrifugal chuck apparatus according to claim 1 wherein said trunnion shaft body comprises:

a body member symmetrically situated around said hollow drive shaft; and a trunnion shaft into which said throughbore is formed and which is fixedly joined to diametrically opposed sides of said body member.

5. A centrifugal chuck apparatus according to claim 1 further comprising a predetermined weight member at the distal end of each lever arm.

6. A centrifugal chuck apparatus according to claim 3 further comprising:

said trunnion body, said first and second lever arms and said first and second leaf spring members all formed as a single unit.

7. A method for coaxially securing a tool shaft of a surgical instrument within the hollow drive shaft of a handpiece comprising the steps of:

providing a trunnion body having a transverse axis and a throughbore transversely oriented with respect to said transverse axis, said throughbore having a longitudinal axis and being for receiving the tool shaft therethrough;

pivotably attaching said trunnion body within said drive shaft to enable said throughbore longitudinal axis to be substantially coaxial with the axis of said drive shaft in response to centrifugal force;

securing to diametrically opposing lateral sides of said trunnion body a lever arm and extending said lever arms in opposite directions from each other to apply a centrifugal force to said trunnion body about its axis upon rotation of said drive shaft;

inserting a tool shaft into said drive shaft and said throughbore; and rotating said drive shaft to pivot said trunnion body about its axis to thereby centrifugally secure said tool within said drive shaft.

8. A method according to claim 7 further comprising the step of:

providing a spring member on each of said lever arms to bias said body rotationally to impart to said throughbore axis a predetermined misalignment from said drive shaft axis when said drive shaft is stationary.

9. A method according to claim 7 further comprising the step of:

providing a predetermined weight at the distal end of each lever arm to increase the centrifugal force produced by rotation of said trunnion body about the axis of said drive shaft.

* * * * *